United States Patent
Khoury

(10) Patent No.: US 9,629,685 B2
(45) Date of Patent: Apr. 25, 2017

(54) SURGICAL INSTRUMENT COMPRISING A DETECTION MEANS

(71) Applicant: Wassim Khoury, Paris (FR)

(72) Inventor: Wassim Khoury, Paris (FR)

(73) Assignees: Tagil Family Foundation, Vaduz (LI); Wassim Khoury, Paris (FR)

( * ) Notice: Subject to any disclaimer, the term of this patent is extended or adjusted under 35 U.S.C. 154(b) by 129 days.

(21) Appl. No.: 14/365,541

(22) PCT Filed: Dec. 14, 2012

(86) PCT No.: PCT/EP2012/075667
§ 371 (c)(1),
(2) Date: Nov. 14, 2014

(87) PCT Pub. No.: WO2013/087909
PCT Pub. Date: Jun. 20, 2013

(65) Prior Publication Data
US 2015/0061834 A1 Mar. 5, 2015

(30) Foreign Application Priority Data

Dec. 15, 2011 (FR) ...................................... 11 61694

(51) Int. Cl.
*G01N 33/50* (2006.01)
*B65D 83/10* (2006.01)
(Continued)

(52) U.S. Cl.
CPC .............. *A61B 19/44* (2013.01); *A61B 5/065* (2013.01); *A61B 50/36* (2016.02); *A61B 50/362* (2016.02); *A61B 90/90* (2016.02); *A61B 90/98* (2016.02); *A61B 50/37* (2016.02); *A61B 2090/0805* (2016.02); *A61B 2090/0806* (2016.02)

(58) Field of Classification Search
CPC .............. A61B 19/44; A61B 2019/448; A61B 2090/0805; A61B 5/065; A61B 19/081; A61B 19/5225; A61B 2019/442; A61B 2019/446; A61B 90/96; A61B 90/98; A61B 50/36; A61B 50/37; A61B 90/90; G11B 2007/24306; G11B 2007/2432;
(Continued)

(56) References Cited

U.S. PATENT DOCUMENTS 6,366,206 B1 4/2002 Ishikawa et al.
7,971,715 B1 * 7/2011 Fernandes .............. A61B 90/98
116/100

(Continued)

FOREIGN PATENT DOCUMENTS

| FR | 2937860 A1 | 5/2010 |
|---|---|---|
| WO | WO 96/22510 A1 | 7/1996 |
| WO | WO 2009/003231 A1 | 1/2009 |

*Primary Examiner* — Dionne H Pendleton
(74) *Attorney, Agent, or Firm* — Reinhart Boerner Van Deuren P.C.

(57) ABSTRACT

The invention relates to a surgical instrument (1) comprising a detection means (10) for reacting to at least one external stress (30) emitted by a generator means (15) that generates the stress (30). The invention also relates to the method for producing such a surgical instrument (1). The invention likewise relates to the generator means (15). The invention further relates to a method for detection of the surgical instrument (1) by the generator means (15).

13 Claims, 3 Drawing Sheets

(51) Int. Cl.
    *A61B 19/00*   (2006.01)
    *A61B 50/36*   (2016.01)
    *A61B 5/06*    (2006.01)
    *A61B 90/90*   (2016.01)
    *A61B 90/98*   (2016.01)
    *A61B 90/00*   (2016.01)
    *A61B 50/37*   (2016.01)

(58) Field of Classification Search
    CPC ..... G11B 7/00456; G11B 7/243; G11B 7/253;
            G11B 7/261; A61F 13/44; Y10T 428/21
    See application file for complete search history.

(56) References Cited

U.S. PATENT DOCUMENTS

| | | | |
|---|---|---|---|
| 8,945,376 B1 * | 2/2015 | Cordisco | B01F 11/0002 134/105 |
| 2006/0065739 A1 | 3/2006 | Falls, Jr. et al. | |
| 2007/0125392 A1 | 6/2007 | Olson, Jr. et al. | |
| 2009/0317002 A1 * | 12/2009 | Dein | A61B 19/44 382/224 |
| 2011/0036738 A1 | 2/2011 | Hiltl | |
| 2011/0174877 A1 | 7/2011 | Fleck et al. | |

* cited by examiner

SURGICAL INSTRUMENT COMPRISING A DETECTION MEANS

The field of the invention is that of surgical instruments, in particular for single use, and in particular of compresses.

Gauze compresses, routinely used in medicine and in particular in surgical specialities such as abdominal, gynaecological or thoracic surgery, serve in particular to absorb blood during an operation. A major problem encountered by surgeons and nurses when using such compresses is the risk of leaving one of the compresses in the patient's body. The risk is even greater because once soaked with blood a compress resembles a lump of fat and thus can be difficult to distinguish in the body of a patient.

In order to limit this risk, it is known to count the number of compresses before and after the operation in order to verify that none of them has been left in the patient's body. However, such a verification operation creates a considerable loss of time for the nurses who must count all the compresses before and after the operation, and also for the surgeon who must await the confirmation of the verification in order to terminate his operation and suture the patient. Furthermore, counting compresses at the end of the operation is a delicate operation posing hygiene problems for the practitioners, and in particular the nurses, especially because they handle blood-soaked compresses which may carry numerous diseases.

In the event that a discrepancy is found between the number of compresses before and after the operation, it is necessary to repeat the count and at the same time to verify whether the missing compress or compresses have been inadvertently discarded, for example when the surgeon removes his operating gloves. If the still do not tally, the surgeon then has to look carefully in the patient's body to search for the compress which, as was previously stated, can easily be confused with a lump of fat. Thus it will be understood that the use of surgical instruments creates practical management difficulties.

In order to verify that the count has been properly carried out or for the purpose of ensuring that the missing compress or compresses are not in the patient's body, it is known to dispose on the compress, at the time of manufacture, a radio-opaque baryte wire in order to render them visible to X-rays. Such compresses comprising a baryte wire are therefore detectable using X-ray radiographs, usually taken several hours after each operation.

A first drawback relating to this solution is that the resolution of the radiography system used must be very high in order to detect the baryte wire. The principal drawback of this method results from the fact that it takes place after the operation, that is to say once the patient has been sutured or closed up. In this case, it is then necessary to re-operate, with all the drawbacks of a new intervention for the patient, that is to say with all the risks that surgery may cause for the patient who has just already undergone an operation, which may be a major operation, and the risks are even greater if the patient is old or has health problems.

In the event that the radiograph is not of good quality and therefore does not make it possible to detect the baryte wire and the compress, the consequences for the patient may be even more serious, as the compress can in particular cause an infection.

Whether or not the oversight is diagnosed quickly, this may have dramatic consequences for the patient, as has been seen above, but also for the hospital and the practitioner responsible. This may in fact give rise to serious financial losses for the hospital due to the new operation and possible legal proceedings.

Thus the invention seeks to improve the situation.

To this end it first of all proposes a surgical instrument comprising a detection means suitable for reacting to at least one external prompt emitted by a means for generating the prompt.

It will be understood here that the prompt is external to the detection means. The prompt is, for example, a signal, in particular a radio frequency signal. Following this external prompt, the detection means reacts for example by sending a signal, otherwise referred to as a reaction, thus rendering it detectable by the generator means.

Thus, by virtue of the invention, the surgical instrument is detectable at all times, that is to say before, during and after the operation. The surgical instrument is also detectable instantaneously, for example within several seconds or several minutes. The practitioner or the nurse passes the generator means close to the patient, the detection means reacting to a prompt emitted by the generator means. In other words, if nothing happens, there is no detection means and therefore no surgical instrument. On the other hand, if the detection means reacts, its reaction is detected by the generator means and thus gives the information that a surgical instrument is located in the checked zone, known as the monitoring zone.

Such a method of detection can also be transposed into a situation where the surgical instruments are detected and counted prior to the surgery, and where a container in which the surgical instruments have been collected is checked after the surgical intervention with a view to providing the practitioner with information comparing the detection prior to the surgery and the checking after the surgery. Such detection and such checking is carried out by the generator means.

Advantageously, said surgical instrument is for single use. Single use is understood to mean that the surgical instrument is intended to be used just once, for example during a single surgical intervention. The surgical instrument for single use is sterile and is discarded after the surgical intervention.

According to an aspect of the invention, the detection means is capable of reacting to radio frequencies. Advantageously, the detection means is a RFID tag. The RFID tag is arranged in order to receive and respond to the prompt, and thus to render detectable the surgical instrument to which it is fitted. The generator means is for example a detector/emitter of radio frequencies.

In an embodiment of the invention, the detection means comprises a device for rigid connection to the surgical instrument. Thus the detection means can thus be rigidly connected to the surgical instrument, for example at the time of production of the surgical instrument. Advantageously, said rigid connection device comprises a material suitable for stamping. Thus the detection means can be hot-stamped for example. Advantageously, the material suitable for stamping is a polymer disposed at least on a periphery of the detection means. The material suitable for stamping is polyurethane or silicone for example.

Alternatively, said rigid connection device comprises an adhesive material. Advantageously, said rigid connection device comprises an adhesive strip. Advantageously, the adhesive material and/or the adhesive strip is applied to a flat surface of the detection means. Thus the detection means can be stuck to the surgical instrument.

According to an aspect of the invention, the detection means is disposed in the region of a periphery of said surgical tool.

According to an embodiment of the invention, the surgical instrument is a compress, in particular a gauze compress. The detection means is disposed for example on a periphery of the compress. In this way, when the compress is folded, for example in order to be packaged or in order to adapt to the area of the patient to which it will be applied, there is no risk of the detection means disrupting the folding since it will not be located in a zone which might disturb the packaging operation or the use of the compress.

Advantageously the detection means is rigidly connected within a fold of the compress, in particular a fold situated on a periphery of the compress. Thus the detection means is surrounded by the compress. In this way the outer faces, that is to say the flat faces, of the detection means are protected. The mechanical stability between the detection means and the compress is also increased.

The invention also relates to a method for producing a surgical instrument as described above, wherein the detection means is joined to the surgical instrument. It is then possible to join the means to the instrument at the time of production of the instrument, for example when the compress is woven. This method for producing the surgical instrument is particularly appropriate if the surgical instrument is for single use.

According to an aspect of the invention, the detection means is stamped on the surgical instrument. It is hot-stamped, for example.

According to an embodiment of the invention, the detection means is stuck to the surgical instrument.

The invention likewise relates to a means for generating a prompt for a reaction from a detection means for detecting surgical instruments, said generator means comprising a means for interpreting said reaction, obtained in response to said prompt, characterised in that said generator means is arranged so as to be detachably fixed to a means for receiving said surgical instruments.

Thus by virtue of the invention said surgical instruments are identified at the moment when they pass in front of the generator means, fixed to the receiving means. By positioning the generator means on the receiving means, and following a surgical intervention, all the surgical instruments discarded of in the receiving means are identified. The removable nature of the generator means also makes it possible to identify the surgical instruments at different places and at different moments in the surgical intervention as explained below.

According to an aspect of the invention, said generator means comprises an antenna for emitting the prompt and/or for receiving the reaction having an opening through which the surgical instrument(s) are intended to pass when they are deposited in the receiving means.

According to an embodiment of the invention, said antenna is in the form of a ring.

According to an aspect of the invention, said antenna is configured in order to be disposed on said receiving means in such a way that it defines a passage of said surgical instruments in said receiving means.

According to an embodiment of the invention, said antenna is configured in order to be disposed on said receiving means in such a way that it defines an entrance for said surgical instruments into said receiving means.

According to an embodiment, said means for generating the prompt is portable. Thus it is possible to move it into specific zones which are to be checked, for example the surgical site or a container for the surgical instruments. Advantageously, said means for generating the prompt has an autonomous electrical power supply and/or a screen for reading the information gathered. The practitioner or the nurse can then pass the generator means around the patient with complete freedom of movement, that is to say without hindrance due to the presence of a power supply wire.

Alternatively, said prompt generator means is configured so that it can be fixed to another support. Said other support is, for example, the floor of an operating theatre, an operating table and/or a lamp for illuminating the operating zone. According to an embodiment, the generator means is a gantry which can be moved around the operating table, or fixed to the entrance of the operating theatre.

According to an embodiment, said means for generating said prompt has a device for identifying the detection means among a plurality of detection means. The detection means comprises a single identification which makes it possible to identify it among other detection means, the generator means being capable of distinguishing between the surgical instruments bearing detection means of which the reaction is different from one means to the other.

The invention also relates to an assembly comprising a generator means as described above and a means for receiving surgical instruments.

The invention likewise relates to a system comprising a surgical instrument and a generator means as described above.

As already stated, said prompt generator means may comprise a means for interpreting a reaction coming from the detection means in response to the prompt. Thus the detection means is capable of receiving a prompt and emitting a reaction in response to this prompt. The reaction is, for example, a signal. Thus said generator means is capable of generating the prompt and interpreting the reaction of said detection means in response to the prompt in order to communicate information to the practitioners.

The invention also relates to a method for detecting a surgical instrument by a generator means, said generator means and said surgical instrument forming a system as described above, in which method:
  the prompt is generated in the direction of a monitoring zone,
  the detection means present in the monitoring zone each emit a reaction in response to the prompt,
  the reaction(s) of the detection means are detected.

This method of detecting the surgical instrument is particularly appropriate in the case where the surgical instrument is for single use.

In a particular embodiment of the method of detection:
  the generator means is moved around the monitoring zone.

According to an aspect of the invention, the monitoring zone is an area on which the patient is to undergo surgery. Thus it is possible to detect the detection means located in the intervention zone and in particular to identify it precisely by virtue of the identification device of the generator means.

Alternatively:
  with the aid of the generator means all the surgical instruments carrying a detection means are identified prior to the surgery,
  all the surgical instruments are checked after the surgical intervention, in particular by disposing them in the monitoring zone, with the aid of the generator means,
  the generator means compares the identification prior to the surgery and the checking subsequent to the surgery and communicates information to the practitioner.

The monitoring zone is for example the receiving means, in particular a container into which all the surgical instruments are discarded once they have been used. By virtue of the identification device of the generator means, each of the detection means present in the monitoring zone and therefore each of the surgical instruments is identified precisely. Thus it is possible to detect whether or not all of the surgical instruments used during the surgical intervention are present.

Where the monitoring zone is the receiving means, the method of detection according to the invention provides a step in which the generator means is disposed on the receiving means for surgical instruments in such a way that they form the assembly according to one of Claims 4 or 5.

The surgical instruments can then be directly identified at the moment when they are discarded in the receiving means or identified at the moment when the generator means is positioned on the receiving means.

According to an embodiment,
the step of identification prior to the surgical intervention is effected by generating the prompt in the direction of at least one pack containing all the surgical instruments intended to be used during the surgical intervention.

It is then possible to compare the number of surgical instruments before and after the surgery and to detect the identification of the missing surgical instrument(s).

The detachable nature of the fixing of the generator means to the receiving means enables the generator means to perform this comparison. It likewise enables it to identify, somewhere other than in the receiving means, a surgical instrument which may be missing during the comparison performed before and after the surgery.

Other characteristics and advantages of the invention will become clearer by reading the following description of an embodiment of the surgical instrument described in the invention with reference to the appended drawings, in which.

Figure 1:
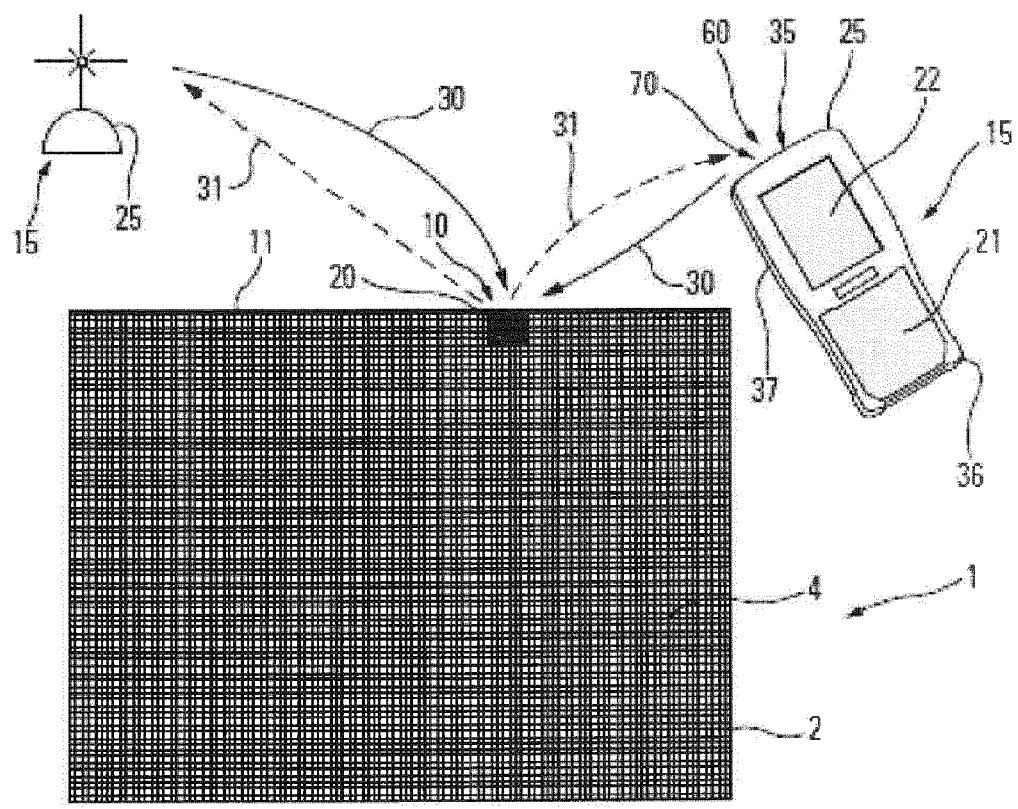
FIG. 1 shows a schematic plan view of a surgical instrument, in particular a compress comprising a detection means capable of reacting to a prompt, and a means which generates the prompt.
Figure 3:
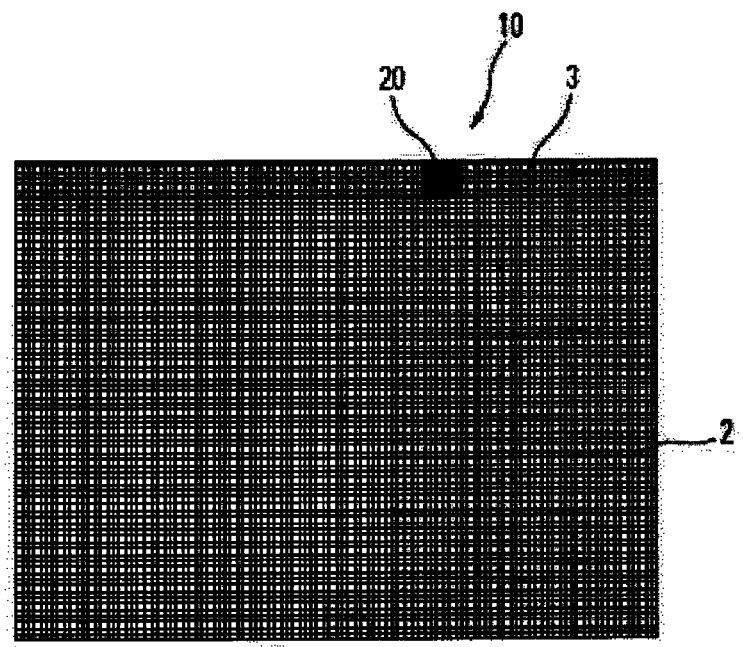
FIG. 3 shows a schematic plan view of an alternative embodiment of the compress illustrated in FIG. 1.

FIG. 1 shows a surgical instrument, in particular for single use. According to the invention the surgical instrument 1 comprises a detection means 10 capable of reacting to at least one external prompt 30 emitted by a generator means 15 which generates the prompt 30. The example of a surgical instrument 1 illustrated in FIGS. 1 and 3 is in this case a compress 2, for example of gauze, and in particular sterile. The detection means 10 is configured in order to resist to the methods of sterilisation known at present, for example by gamma or preferably beta rays, or else by methylene oxide. These methods of sterilisation may be carried out to of temperatures substantially below 40° C.

Such a compress 2 comprises a woven fabric of threads 4, for example hydrophilic cotton gauze fibre.

Figure 2:
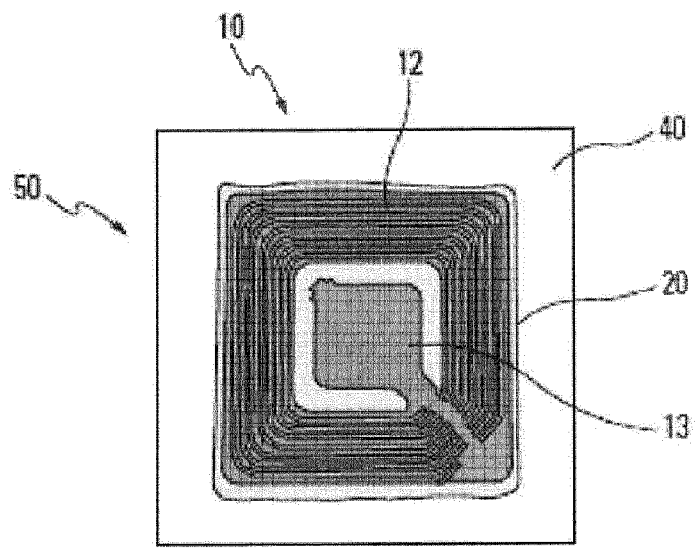
FIG. 2 shows a detailed plan view of the detection means of FIG. 1.

The detection means 10 illustrated in FIG. 1, and in greater detail in FIG. 2, is a RFID tag 20 otherwise referred to as a marker. It comprises an antenna 12 associated with an electronic chip 13 which enable it to react to an external prompt 30, that is to say in this case to receive the prompt 30, to analyse it and to respond thereto. The antenna 12 and the electronic chip 13 are situated, in particular, in the region of a front face of the RFID tag 20.

The prompt 30 is emitted by the generator means 15, in this case a radio frequency reader 25. This is an emitter and a receiver of radio frequencies. The prompt 30 is for example a radio frequency prompt emitted by the radio frequency reader 25. The RFID tag 20 emits a reaction 31, in this case a response signal otherwise referred to as a reaction, in response to the external prompt 30 from the radio frequency reader 25. This is in particular the antenna 12 of the RFID tag 20 which emits the reaction 31. The antenna 12 of the RFID tag 20 is made for example from copper. Thus the detection of the RFID tag 20 by the radio frequency reader 25 is of the radio frequency identification type, more often designated by the acronym RFID (radio frequency identification).

The RFID tags 20 are for example passive devices which do not require any energy source apart from that supplied by the radio frequency reader 25 at the moment of their prompt. One of the reactions is the return of a digital identification, for example that of the EPC-96 standard which uses 96 bits.

The RFID tag 20 according to the invention is situated in particular in the region of a periphery 11 of the surgical instrument 1, that is to say in this case on a periphery of the compress 2. The periphery 11 is understood to mean a zone situated close to an edge of the compress 2. In other words, the RFID tag 20 comprises a strip running along a part of the edge of the compress 2, the rest of the RFID tag 20 being located on the compress 2.

The radio frequency reader 25 is for example an active device emitting the prompt 30 and receiving the reaction 31. The radio frequency reader 25 activates the RFID tag 20 by supplying it here, by means of the prompt 30, with energy which the RFID tag 20 needs in order to react. The frequency used is variable, depending upon the type of application, the performance levels sought and the detection distance targeted. The frequency of use can likewise be fixed, in particular in the case where a portable radio frequency reader 25 is used.

For this the radio frequency reader 25 comprises a device 60 for emitting the prompt 30 which enables it to emit the prompt 30. It also comprises a device 70 for receiving the reaction 31 which enables it to receive the reaction 31. The devices 60 for emitting the prompt 30 and the devices 70 for receiving the reaction 31 comprise in particular one or several antennas (referenced 16 in FIG. 4) by which the prompt 30 is emitted and the reaction 31 is received.

In order to analyse the reaction 31 of the RFID tag 20, the radio frequency reader 25 comprises an interpreting means 35. Thus the interpreting means 35 makes it possible to inform the user, by means of a screen 22, whether or not the RFID tag 20 is present in the checked zone, in particular in the intervention zone, that is to say a zone situated around and above the patient.

The radio frequency reader 25 has an autonomous electrical power supply 36, for example an electric battery. It also comprises a control zone 21 from which the user of the radio frequency reader 25 can in particular control the emission of the prompt 30.

The radio frequency reader 25 may be portable as illustrated at top right in FIG. 1 or fixed to a support as shown at top left in FIG. 1. In the case where it is portable, it can be moved simply around the patient or close to any zone which is to be checked, for example at a distance of less than 40 cm from the zone which is to be checked, wherein this distance can be reduced until the radio frequency reader 25 makes contact with the patient, in this case using transparent sterile pockets disposed between the patient and the radio frequency reader 25. If it is portable, it can likewise be detachably fixed to a receiving means as explained below.

In the case where the radio frequency reader 25 is fixed to a support, the support may advantageously be the operating table or else a light for illuminating the area to be operated upon, in such a way that the radio frequency reader 25 is located close to the patient and the surgical intervention zone and that it can emit the prompt in the direction of this zone for the purpose of detecting the RFID tag 20. In the case where the radio frequency reader 25 is fixed to a support, it should be situated at a distance, for example equal to a meter from the zone which is to be checked.

Regardless of whether it is portable or fixed to a support, the radio frequency reader 25 has a device 37 for identifying the RFID tag 20. The reaction 31 of the RFID tag 20 being in particular a digital identification which uses 96 bits, each RFID tag 20 comprises its own digital identification. Thus the identification device 37 makes it possible to identify precisely the number of the RFID tag 20 and therefore of the compress 2 on which it is situated. As the compresses 2 are arranged in series, for example in series of ten compresses, each series being present before the operation in separate packs, it is possible to know the pack to which it belonged and therefore to know at what point during the operation it was used by identifying the number of the compress 2 using the RFID tag 20. In the event of the compress 2 being forgotten, it is thus possible to limit the visual search for the compress 2 to the area of the patient's body operated on at the point when the compress was used.

According to an alternative embodiment, the RFID tags 20 are in particular active devices. In this case they comprise their own source of energy. Therefore in this case they do not need to receive energy from the radio frequency reader 25. In this alternative embodiment, the radio frequency reader 25 therefore does not supply any energy to the RFID tag 20.

The RFID tag 20 is resistant to humidity and up to temperatures substantially equal to 200° C. It is in particular covered and protected by two films which are resistant to humidity and to temperatures ranging up to substantially 200° C. The two films are made for example from flexible polymer material, in particular polyurethane. The RFID tag 20 is extremely discreet due to its fineness, for example several tenths of a millimeter, its reduced size, in particular several millimeters, and its negligible mass. The RFID tag 20 has for example a length of approximately 30 mm and a width of approximately 10 mm. Its cost is minimal. It also comprises specific characteristics which render it flexible and impermeable. It is for instance because of its low thickness and the material of which it is constituted, in particular its copper antenna and its flexible polymer protective films, that the RFID tag 20 is flexible. This characteristic is important because of the need for the compress 2 to be flexible in order in particular to be arranged in different ways in order to best suit the area to which it will be applied. Such an RFID tag 20 is then perfectly adapted in order to be incorporated into the compress 2 or into another surgical instrument and to be in contact in particular with the blood or any other liquids present in the body of the patient, without risk of being damaged and without risk of significantly altering the intrinsic characteristics of the compress, in particular absorption.

The RFID tag 20 comprises a device 50 for rigid connection to the compress 2. This rigid connection device 50 is situated for example on a rear face of the RFID tag 20, that is to say the opposing face comprising the chip and the antenna.

The joining device 50 can also extend beyond a periphery of the RFID tag 20, in particular over all of the periphery of the RFID tag 20, that is to say all around the RFID tag 20. The joining device 50 then forms a peripheral strip of the RFID tag 20.

The joining device 50 comprises, in this case, a material 40 capable of being stamped on the compress 2, such a material being for example thermo-compressed on the compress. The material 40 capable of being stamped on the compress 2 is in particular a polymer and for example a polyurethane or a silicone. It is intended to melt when hot, that is to say at approximately 200° C., and to solidify when cold. In a first variant the material becomes adhesive. In another variant, it mingles with the threads 4 so as to form a mechanical link to the compress 2.

In an alternative embodiment of the invention, the joining device 50 comprises an adhesive material, for example glue or silicone. Adhesive material is understood to be a material enabling the RFID tag 20 to be glued to the compress 2. It is for example applied against a flat face of the RFID tag 20, in particular a rear face of the RFID tag 20 intended to be in contact with the compress 2, that is to say a face opposite the front face of the RFID tag receiving the antenna and the chip. According to another alternative embodiment of the invention, the joining device 50 comprises an adhesive strip. An adhesive strip is understood to be a self-adhesive strip comprising two self-adhesive sides, a first one disposed against the rear face of the RFID tag 20 and a second making it possible to glue the RFID tag 20 to the compress.

FIG. 3 illustrates an embodiment of the invention according to which the RFID tag 20 is situated in a fold of the compress 2, in particular a peripheral fold 3 of the compress 2. A peripheral fold 3 is understood to be a fold situated in the region of a periphery of the compress 2. The peripheral fold 3 has for example the width of the RFID tag 20 in such a way that it completely covers the RFID tag 20. The RFID tag 20 is then protected from the external environment since it is located within the compress 2. Its mechanical connection to the compress is likewise improved since the joining device can adhere to the compress 2 and on the peripheral fold 3 of the compress.

Figure 4:
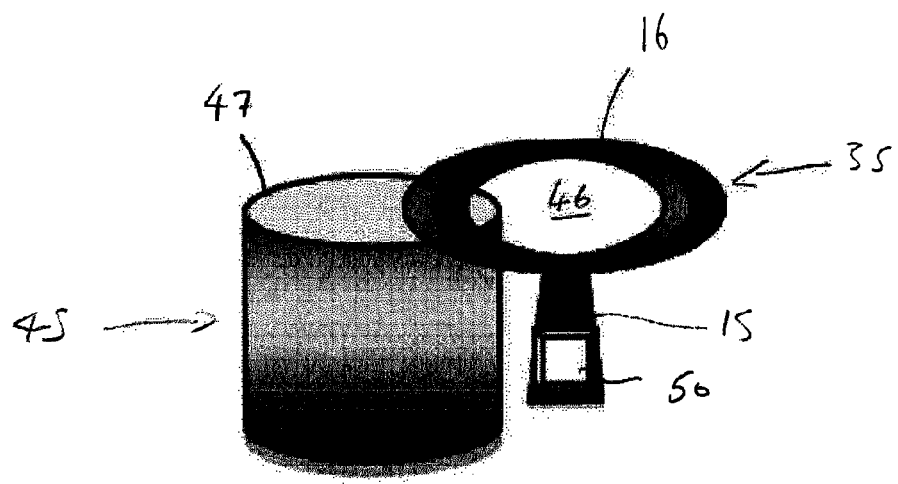
FIG. 4 is a schematic perspective view of the generator means and a receiving means forming an assembly according to the invention.

FIG. 4 illustrates the assembly according to the invention comprising the generator means 15 and the means 45 for receiving the surgical instruments. The receiving means 45 is in this case a bin or basket into which the surgical instruments are discarded after having been used in a surgical operation.

The receiving means is made for example from non-metal material, in particular from cardboard or from plastic. In this case it is cylindrical in shape and has a diameter of 40 centimeters.

According to the invention, the generator means 15 is arranged in order to be detachably fixed to the receiving means. In this way, it can be moved or fixed to the receiving means as required.

Said receiving means 45 may have a supporting frame for a disposable container intended to receive said surgical instruments, in particular said compresses, said generator means 15 then being configured in order to be detachably fixed to said frame.

The antenna 16 of the generator means in this case comprises an opening 46 and is in the form of a ring. The surgical instrument(s) are then intended to pass through the opening 46 when they are deposited in the receiving means 45 and can thus be identified by the generator means 15 by virtue of the detection means 10.

The antenna 16 of the generator means 15 is advantageously disposed on the receiving means 45 in such a way that it defines a passage for the surgical instruments into the receiving means 45. It will be understood in this case that the surgical instruments are intended to pass into a monitoring zone of the antenna 16 which enables them to be identified when they are discarded into the receiving means 45.

In particular, the antenna 16 is disposed on the receiving means 45 in such a way that it defines an entrance for the surgical instruments into the receiving means 45. It is then disposed on a peripheral edge 47 of the receiving means 45.

Said generator means 15 may include a reader for the information gathered. Said reader 50 is situated for example radially.

This being the case, said generator means 15 is advantageously configured in order to exhibit a stability of position once it is in place on the receiving means 45. It may in particular have a centre of inertia intended to be located in the region of the area through which the surgical instruments pass.

Figure 5:
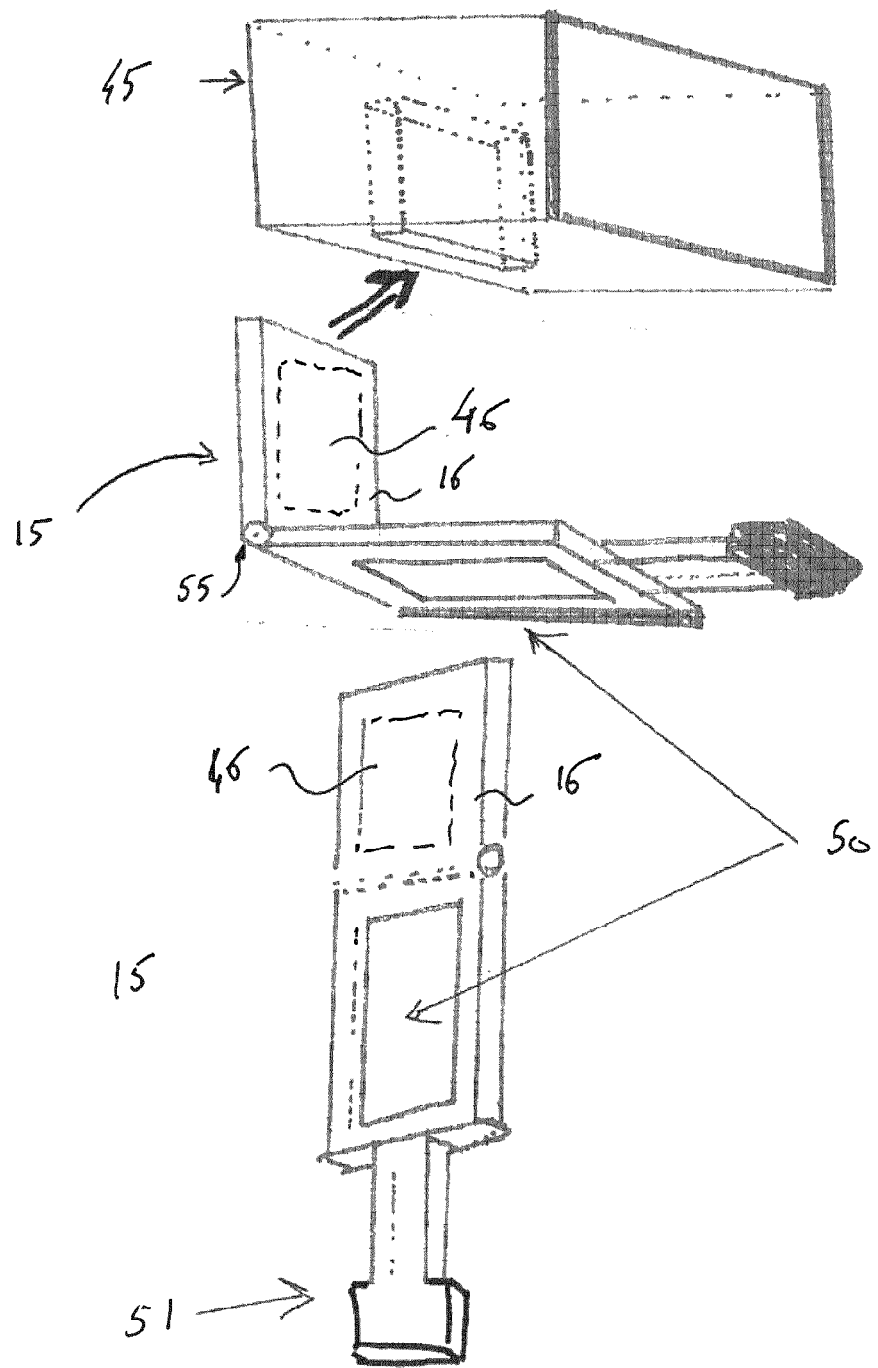
FIG. 5 illustrates a variant of FIG. 4, said generator means being in a folded position where they are intended to be placed on the receiving means and an unfolded position of use.

As illustrated in FIG. 5, it may comprise two parts which are removable with respect to one another, in particular by means of a hinge 55. The first of said parts comprises in particular the antenna 16 and/or the opening 46. Said second part comprises in particular the reader 50 which may or may not be extended by a handle 51.

Such a generator 15 may be configured in order to be positioned in the region of a receiving means 45 such as a basket with drawers.

The invention also relates to a method of manufacturing a surgical instrument 1, wherein the detection means is connected to the instrument 1. It is connected in particular by means of the connecting device 50. In this case the RFID tag 20 is connected to the compress 2, in particular on the periphery 11 and/or in the peripheral fold 3 of the compress 2. In this latter case, the RFID tag 20 is then connected to the compress 2 before or after creation of the peripheral fold 3 which comes to cover the RFID tag 20.

The method according to the invention provides that the detection means 10 is stamped onto the compress 2 in order to connect it to this latter. It is for example hot-stamped. The detection means 10 then comprises the material 40 suitable for stamping. The stamping takes place in particular on the production line for the woven fabric of the compress 2 in such a way that the method of manufacture of the compress 2 is not or is hardly slowed down.

The method according to the invention provides an alternative embodiment according to which the detection means 10 is connected to the compress 2 by adhesion in order to connect it to this latter. The detection means 10 then comprises, as seen above, the adhesive material and/or the self-adhesive strip. In this case also, the adhesion takes place in particular on the production line of the woven fabric of the compress 2 in such a way that the method of manufacture of the compress 2 is not or is hardly slowed down.

According to a variant of the invention, the RFID tag 20 is integrated into the compress 2 during the weaving of the compress 2. The threads 4 are for example stitched on the rigid connection device 50, wherein this latter may be adhesive or lack this adhesive character.

Following the connection of the detection means 10 on the compress 2, the compress 2 is cut out then folded before being packed.

The invention further relates to a method for detecting the surgical instrument 1 by the generator means 15, wherein:
the prompt 30 is generated in the direction of a monitoring zone,
the detection means present in the monitoring zone each emit a reaction 31 in response to the prompt 30,
the reaction(s) 31 of the detection means 10 are detected.

If the generator means 15 is portable, as illustrated in FIG. 1, it is moved close to the monitoring zone which is to be checked, that is to say close to the zone where one or more detection means are to be identified. In the case where the generator means 15 is connected to a fixed support, the generator means 15 can then emit the prompt 30 towards a specific zone, all detection means 10 passing through this zone then being detected. This is the case for example for a generator means connected to the floor at the entrance to the operating theatre.

The monitoring zone is for example the surgical intervention zone, that is to say a zone in which the surgical instrument 1 is used, in particular the zone in which the patient is located. Thus it is possible to detect directly whether or not the detection means 10 is present on the patient.

According to a variant of the invention,
all the surgical instruments 1 intended to be used in the course of a forthcoming surgical intervention are positioned in the monitoring zone,
the generator means identifies these surgical instruments,
all the surgical instruments present in the monitoring zone are checked after the surgery, the generator means then supplying information for the attention of the practitioner in order indicate to him whether the result of the comparison is equal to zero or not.

The monitoring zone is for example a container into which all the surgical instruments used during the surgical intervention are discarded. By then moving the portable generator means 15 close to the container, or by moving the container close to the fixed generator means, the generator means identifies precisely all the detection means present and therefore all the surgical instruments present in order to verify that none of them is missing with respect to the identification carried out prior to the surgical intervention.

In order to be able to identify and compare the number of detection means 10 before and after the surgical intervention, the invention also provides that the prompt 30 is generated towards at least one pack containing a plurality of or all of the surgical instruments 1 intended to be used during the surgical intervention. This is for example the case of a pack containing ten compresses.

The invention has been described by means of the drawings on which an embodiment of a surgical instrument 1 is illustrated, in this case the compress 2. It is obvious that the invention applies to all types of surgical instruments, in particular plastics forceps known as "vascular clips", scissors, or else compresses of larger dimensions referred to as "abdominal drapes", advantageously for single use. It is then possible to rigidly connect the detection means to the surgical instrument according to one of the examples seen previously or for example by embedding the detection means in a plastic material constituting a part of the surgical instrument 1 according to the invention.

In the same way, the invention has been described with the aid of the drawings taking a RFID tag 20 as an example of detection means 10, and a radio frequency reader 25 as an example of generator means. It is obvious that the invention relates to other types of detection means 10 capable of reacting to a prompt emitted by another type of generator means.

The invention claimed is:

1. Means (15) for generating a prompt (30) for a reaction from a means for detecting surgical instruments, said generator means comprising a means (35) for receiving said reaction (31), obtained in response to said prompt (30), characterised in that said generator means (15) is arranged so as to be detachably fixed to a means (45) for receiving said surgical instruments (1);
   wherein said generator means (15) comprises an antenna (16) for emitting the prompt and/or for receiving the reaction, which antenna has an opening (46) through which the surgical instrument(s) (1) are intended to pass when they are deposited in the receiving means (45); and
   wherein said generator means (15) for generating the prompt (30) is portable.

2. Generator means (15) according to claim 1, wherein the antenna (16) is in the form of a ring.

3. An assembly comprising: a generator means (15) according to any of the preceding claims and a means (45) for receiving surgical instruments (1).

4. An assembly according to claim 3, wherein said antenna (16) is disposed on said receiving means (45) in such a way that it defines a passage for said surgical instruments (1) into said receiving means (45).

5. An assembly according to claim 4, wherein said antenna (16) is disposed on said receiving means (45) in such a way that it defines an entrance for said surgical instruments (1) into said receiving means (45).

6. A surgical instrument (1) comprising: a detection means (10) suitable for reacting to at least one external prompt (30) emitted by the means (15) for generating said prompt according to any of claim 1 or 2.

7. A surgical instrument (1) according to claim 6, wherein the detection means (10) comprises a device (50) for rigid connection to the surgical instrument (1) comprising an adhesive strip.

8. A surgical instrument (1) according to claim 6, wherein the surgical instrument (1) is a compress (2), said detection means (10) being rigidly connected in a fold (3) of the compress (2).

9. A system comprising: the means (15) for generating the prompt (30) according to any of claim 1 or 2; and
   a detection means (10) suitable for reacting to at least one external prompt (30) emitted by the means (15) for generating said prompt.

10. A system according to claim 9, wherein said generator means (15) for generating the prompt (30) comprises a device (37) for identifying the detection means (10) from among a plurality of detection means (10).

11. Method for detecting at least one surgical instrument (1) by means of a generator means (15), said generator means (15) and said surgical instrument (1) forming a system according to claim 9, in which method:
    the prompt (30) is generated in the direction of a monitoring zone,
    the detection means (10) present in the monitoring zone each emit a reaction (31) in response to the prompt (30),
    the reaction(s) 31 of the detection means (10) are detected.

12. Detection method according to claim 11, wherein the monitoring zone is the receiving zone (45) and wherein:
    the generator means (15) is disposed on the receiving means (45) for surgical instruments (1) in such a way that they form the assembly.

13. Detection method according to claim 11, wherein:
    all the surgical instruments (1) carrying a detection means (10) are checked prior to the surgical intervention with the aid of the generator means,
    all the surgical instruments (1) are checked after the surgical intervention, in particular by disposing them in the monitoring zone, with the aid of the generator means (15),
    the generator means (15) compares the identification prior to the surgery and the checking subsequent to the surgery and communicates information.

* * * * *

UNITED STATES PATENT AND TRADEMARK OFFICE
CERTIFICATE OF CORRECTION

PATENT NO. : 9,629,685 B2  
APPLICATION NO. : 14/365541  
DATED : April 25, 2017  
INVENTOR(S) : Wassim Khoury Page 1 of 1

It is certified that error appears in the above-identified patent and that said Letters Patent is hereby corrected as shown below:

In the Claims

Column 11, Line 25, Claim 3:
After the word comprising delete ":"

Column 11, Line 36, Claim 6:
After the word comprising delete ":"

Column 11, Line 39, Claim 6:
Delete "claim" and replace with --claims--

Column 12, Line 5, Claim 9:
After the word comprising delete ":"

Column 12, Line 6, Claim 9:
Delete "claim" and replace with --claims--

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*